United States Patent
D'Alelio

[11] 3,980,737
[45] Sept. 14, 1976

[54] HALOGENATED ESTERS OF PHOSPHORUS-CONTAINING ACIDS

[76] Inventor: Gaetano F. D'Alelio, 2011 E. Cedar St., South Bend, Ind. 46617

[22] Filed: Jan. 9, 1975

[21] Appl. No.: 539,813

Related U.S. Application Data

[60] Division of Ser. No. 383,583, July 30, 1973, Pat. No. 3,886,236, which is a continuation-in-part of Ser. No. 179,543, Sept. 10, 1971, Pat. No. 3,780,144, which is a continuation-in-part of Ser. No. 785,335, Dec. 19, 1968, abandoned.

[52] U.S. Cl. .............................................. 260/952
[51] Int. Cl.² .......................................... C07F 9/48
[58] Field of Search ................................. 260/952

[56]         References Cited
         UNITED STATES PATENTS

| | | | |
|---|---|---|---|
| 2,929,831 | 3/1960 | Ackerman et al. | 260/952 |
| 3,030,347 | 4/1962 | O'Brien et al. | 260/952 X |

FOREIGN PATENTS OR APPLICATIONS

| | | | |
|---|---|---|---|
| 43-8092 | 3/1968 | Japan | 260/952 |

*Primary Examiner*—Richard L. Raymond
*Attorney, Agent, or Firm*—Walter J. Monacelli

[57] ABSTRACT

This invention deals with new phosphorus-containing esters having the formulas

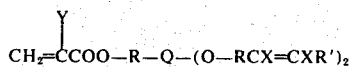
and
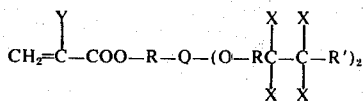

wherein
Y represents H, CH₃ or Cl;
R repesents a divalent hydrocarbon radical containing one to twenty carbon atoms;

Q represents >P— or —P<;

R' repesents X, hydrogen or R'';
R'' represents a monovalent hydrocarbon radical containing one to twenty carbon atoms; and
X represents chlorine or bromine.

These new esters are useful particularly as fire retardants, agricultural chemicals, fuel additives, plasticizers, monomers and intermediates for the synthesis of other useful derivatives.

14 Claims, No Drawings

HALOGENATED ESTERS OF PHOSPHORUS-CONTAINING ACIDS

This application is a division of application Ser. No. 383,583, filed July 30, 1973, now U.S. Pat. No. 3,886,236, which in turn is a continuation-in-part of application Ser. No. 179,543, filed Sept. 10, 1971, issued as U.S. Pat. No. 3,780,144 on Dec. 18, 1973, which in turn is a continuation-in-part of application Ser. No. 785,335, filed Dec. 19, 1968, now abandoned.

BACKGROUND OF THE INVENTION

1. Field of the Invention

This invention involves new esters containing both phosphorus and halogen atoms in their structures. More specifically, it concerns the phosphite and phosphonium esters of halogenated acetylenic alcohols.

2. Related Prior Art

No pertinent prior art is known. Some of the intermediate acetylenic phosphorus-containing esters which can be halogenated to some of the products of this invention are disclosed in my copending application, Ser. No. 692,638, filed Dec. 22, 1967, now abandoned.

STATEMENT OF THE INVENTION

The esters of this invention are represented by the formulas:

$$CH_2=\overset{Y}{\underset{}{C}}COO-R-Q-(O-RCX=CXR')_2$$

and $$CH_2=\overset{Y}{\underset{}{C}}-COO-R-Q-(O-R\overset{X}{\underset{X}{C}}-\overset{X}{\underset{X}{C}}-R')_2$$

wherein

Y represents H, $CH_3$ or Cl;

R represents a divalent hydrocarbon radical containing one to twenty carbon atoms;

Q represents

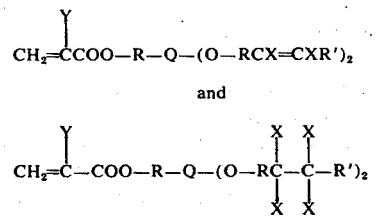

R' represents X, hydrogen or R'';

R'' represents a monovalent hydrocarbon radical containing one to twenty carbon atoms; and X represents chlorine or bromine.

By substitution of the Q in the formulas by either P or P(O) these esters may be represented more specifically by the formulas $$CH_2=\overset{Y}{\underset{}{C}}COO-R-P(O-R-CX=CXR')_2 \quad (A)$$

$$CH_2=\overset{Y}{\underset{}{C}}COO-R-P(O-R-CX_2CX_2R')_2 \quad (B)$$

For many of the purposes of this invention the esters of formula are much preferred because of their greater stability in the attachment of the halogen atoms as discussed more fully hereinafter. However, where higher halogen content is desired, the esters of formula B have particular value for many purposes. Moreover, loss of halogen from the higher substituted type of esters results in the more stable unsaturated form.

The divalent hydrocarbon radical represented by R in the above formulas can be aliphatic, cycloaliphatic or aromatic and can be saturated or have ethylenic or acetylenic unsaturation therein. Aliphatic radicals include aryl-substituted aliphatic radicals such as phenylethylene, phenylenedimethylene, etc.; aromatic radicals include alkyl, alkenyl and alkynyl substituted aromatic radicals such as tolylene, xylylene, ethylphenylene, vinylphenylene, propargylphenylene, etc.; and cycloaliphatic radicals include alkyl, alkenyl, alkynyl and aryl substituted cycloaliphatic radicals such as ethylcyclohexylene, vinylcyclohexylene, propargylcyclohexylene, phenylcycloheptylene, tolylcyclopentylene, etc. The simpler and smaller of these radicals are preferred for obvious reasons, but the more complicated radicals can also be used and are included in the scope of this invention.

These divalent hydrocarbon radicals are illustrated by the following typical radicals: $-CH_2-$; $-(CH_2)_2-$; $-(CH_2)_4-$; $-(CH_2)_7-$; $-(CH_2)_{12}-$; $-C(CH_3)_2-$; $-CH(CH_3)-$; $-CH(C_6H_5)-$; $-CH(C_6H_{11})-$; $-CH(C_4H_9)-$; $-CH(C_8H_{17})-$; $-CH_2CH(C_6H_5CH_3)-$; $-CH(CH_3)CH_2CH_2-$; $-CH_2CH=CHCH_2-$; $-CH_2C\equiv CCH_2-$; $-CH_2CH(CH=CH_2)-$; $-CH(C\equiv CH)CH_2-$; $-CH(CH_2C_6H_5)CH_2-$; $-CH_2C_6H_4CH_2-$; $-CH_2CH_2C_6H_4-$; $-C_6H_4-$; $-C_6H_3(CH_3)-$; $-C_{10}H_6-$; $-C_{10}H_5(C_2H_5)-$; $-C_6H_3(CH=CH_2)-$; $-C_6H_3(CH_2C\equiv CH)-$; $-C_6H_4-C_6H_4-$; $-C_6H_4(C_6H_5)-$; $-C_6H_{10}-$; $-C_5H_8-$; $-C_7H_{12}-$; $-C_6H_9(CH_3)-$; $-C_6H_9(C_6H_5)-$; $-C_6H_9(CH=CH_2)-$; $-C_7H_{11}(CH_2C\equiv CH)-$; $-CH_2C_6H_{10}CH_2-$; $-CH_2CH_2C_6H_{10}-$; $-(CH_2)_8CH=CH(CH_2)_{10}-$; and the like.

The monovalent hydrocarbon radical represented by R'' in the above formulas can be aliphatic, cycloaliphatic or aromatic and can be saturated or have ethylenic or acetylenic unsaturation therein. Aliphatic radicals include aryl-substituted aliphatic radicals such as phenylethyl, diphenylethyl, benzyl, tolylethyl, etc.; aromatic radicals include alkyl, alkenyl and alkynyl substituted aromatic radicals such as tolyl, xylyl, ethylphenyl, vinylphenyl, propargylphenyl, etc.; and cycloaliphatic radicals include alkyl, alkenyl, alkynyl and aryl substituted cycloaliphatic radicals such as ethylcyclohexyl, vinylcyclohexyl, propargylcyclohexyl, phenylcycloheptyl, tolylcyclopentyl, etc. The simpler and smaller of these radicals are preferred for obvious reasons, but the more complicated radicals can also be used and are included in the scope of this invention.

These monovalent hydrocarbon radicals are illustrated by the following typical radicals: $-CH_3$; $-C_2H_5$; $-C_4H_9$; $-CH=CH_2$; $-(CH_2)_7CH_3$; $-(CH_2)_{12}CH_3$; $-CH(CH_3)_2$; $-CH(C_6H_5)_2$; $-CH_2CH=CH_2$; $-CH_2C\equiv CH$; $-CH_2C_6H_{11}$; $-CH_2CH_2C_6H_5CH_3$; $-CH(CH_3)CH_2CH_3$; $-CH_2CH_2CH=CH_2$; $-CH(C\equiv CH)CH_3$; $-CH(CH_2C_6H_5)CH_3$; $-CH_2C_6H_4CH_3$; $-CH_2CH_2C_6H_5$; $-C_6H_5$; $-C_6H_4CH_3$; $-C_6H_3(CH_3)_2$; $-C_{10}H_7$; $-C_{10}H_6C_2H_5$; $-C_6H_4CH=CH_2$; $-C_6H_4CH_2C\equiv CH$; $-C_6H_4-C_6H_5$; $-C_6H_4C_6H_5)$; $-C_6H_{11}$; $-C_5H_9$; $-C_7H_{13}$; $-C_6H_{10}CH_3$; $-C_6H_{10}C_6H_5$; $-C_6H_{10}CH=CH_2$; $-C_7H_{12}CH_2C\equiv CH$; $-CH_2C_6H_{10}CH_3$; $-CH_2CH_2C_6H_{11}$; $-(CH_2)_8CH=CH(CH_2)_9CH_3$; and the like.

The esters of Formula A are prepared by the reaction of one mole of $PX_3$ with one mole of

and the resultant

is reacted with two moles of HO-R-CX=CXR' to give

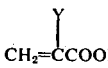 (A)

The esters of Formula B are prepared by using HO-R-$CX_2CX_2R'$ instead of HO-R-CX=CXR' in the reaction of the preceding paragraph.

The above reactions are advantageously conducted in the temperature range of 0° to 100° C., and preferably in the presence of a polymerization inhibitor of the various well known types, such as t-butyl catechol. When polymerization inhibitor is omitted the product is generally at least partially polymerized. Preferably a polymerization inhibitor is used during the preparation of the ester so that polymerization may be conducted subsequently either by itself or with copolymerizable vinyl or vinylene monomer such as styrene, alphamethyl styrene, methacrylates, acrylates, maleic anhydride, unsaturated polyesters, etc., or the monomer may be used for various other purposes as indicated herein.

Instead of using the halogenated acetylenic alcohols with the phosphorus halides as shown in the above reactions, the acetylenic alcohol may be converted first to the ester and the acetylenic ester posthalogenated to the desired product. Also instead of the $POCl_3$ which is used in some of the above reactions, there may be used $PCl_5$ or derivatives thereof, and the reaction product obtained hydrolyzed with water to yield the phosphate ester. Ester exchange reactions can also be used to prepare the esters of this invention.

The (—ORCX=CXR') type of esters of this invention differ from the esters of halogenated saturated alcohols, for example (—$OCH_2CHXCH_2X$), having much greater hydrolytic stability of the halogen atoms than the latter type of esters which show a much greater tendency to lose halogen. This loss of halogen occurs under conditions of high humidity, thereby limiting the utility of the specified type of saturated compound.

The novel phosphorus-containing esters of this invention are self-extinguishing when ignited and thus are particularly useful as fire-retardant additives for a host of other materials and compounds, particularly those of a resinous or polymeric nature, for example, when added to polymethyl methacrylate, polystyrene, cellulose acetate, cellulose butyrate, the polyesters, the polyurethanes, rubbers, nylon and others. They can also be used as fire-retardant impregnants for porous bodies, such as paper, wood fiberboard, cork, etc.

As organic compounds containing phosphorus and halogen atoms they are useful also as agricultural chemicals in the fields of insecticides, herbicides, pesticides, etc., as well as gasoline additives to function as metal scavengers for anti-knock gasolines containing organo-lead, -boron or metallo-organo-compounds. Particularly are they useful as chemical intermediates in the synthesis of a host of other useful derivatives. The di- and trihalo compounds can be halogenated further at the ethylenic double bond to produce tetrahalo and pentahalo compounds which have even greater self-extinguishing properties than the dihalo compounds. They are also readily convertible to the mono- and dibasic phosphorus esters. They also add to olefinic double bonds of the unsaturated compounds to yield plasticizers as well as polymerizable monomers. They react with epoxy compounds to produce substituted alcohols which can be used as modifiers of urethane polymers, polyesters, cellulose, etc.

Derivatives prepared from the compounds of this invention also find utility as flame-retardant additives and impregnants, as agricultural chemicals and as fuel additives. In addition, when the parent compounds or derivatives contain functional groups, such as the OH groups, they can be used as modifiers in polymerization reactions or can be reacted with other functional molecules such as with the isocyanates, acid anhydrides, acid chlorides, oxirane compounds, etc., or when they contain an unsaturated olefinic group they can be homopolymerized or copolymerized with other monomers; or when they contain an amide group they can be reacted with aldehydes and polymerized alone or copolymerized with urea or melamine, or their methylol compounds can be reacted with cellulose or wool, etc.

The practice of this invention is illustrated by the following examples. These examples are given merely by way of illustration and are not intended to limit the scope of the invention in any way nor the manner in which the invention can be practiced. Unless specifically indicated otherwise, parts and percentages are given as parts and percentages by weight.

EXAMPLE I

One hundred forty-five parts of 1,2,3-trichloropropene are added to a solution of 106 parts of sodium carbonate dissolved in 900 parts of water and the mixture refluxed for ten hours. The water layer is then separated from the oily layer which is dried over anhydrous sodium carbonate, separated by filtration and distilled. There is obtained 115 parts of 2,3-dichloro-2-propene-1-ol, $ClCH=CClCH_2OH$, (I), b.p. 45°–46° C./1.5 mm; yield 91%.

EXAMPLE II a. To 250 parts of carbon tetrachloride is added 56 parts of propargyl alcohol (A) and to this solution there is added slowly, at room temperature, a solution of 160 parts of bromine in 250 parts of carbon tetrachloride and allowed to react at room temperature for two hours. Then the mixture is heated to 30°–40° C. for 2 hours. The product is distilled to recover the carbon tetrachloride and the 2,3-dibromo-2-propene-1-ol, $BrCH=CBrCH_2OH$, (II), b.p. 51°–52° 0./0.7 mm; yield 93%.

b. Treatment of 1,2,3-tribromopropene with aqueous sodium carbonate by the procedure of Example I yields the same 2,3-dibromo-2-propene-1-ol.

EXAMPLE III

The reaction of 2-methyl-3-butyn-2-ol (B) with NaOCl under an inert atmosphere of nitrogen according to the procedure given in the Bull. soc. chim. (France), p. 1615 (1965) gives an 87% yield of 4-chloro-2-methyl-3-butyn-2-ol,

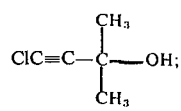

b.p. 54°–56° C./18 mm.

EXAMPLE IV

The reaction of 2-methyl-3-butyn-2-ol in water with $Br_2$ and NaOH by the procedure given in Ann. Chem. (Rome), 47, 118 (1957) yields 4-bromo-2-methyl-3-butyn-2-ol,

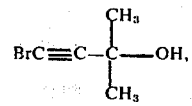

(IV), b.p. 92°–93° C./22 mm.

EXAMPLE V

The procedure of Example II(a) is repeated using instead of propargyl alcohol, one equivalent weight of the following acetylenic alcohols to obtain the halo-derivative corresponding to the alcohol used:

| Acetylenic Alcohol | | Dibromoethylene Derivative | |
|---|---|---|---|
| $HC{\equiv}C{-}\underset{\text{}}{\overset{CH_3}{C}H}{-}OH$ | (C) | $H\overset{Br}{C}{=}\overset{Br}{C}{-}\underset{\text{}}{\overset{CH_3}{C}H}{-}OH$ | (V) |
| $HC{\equiv}C{-}\underset{\text{}}{\overset{C_2H_5}{C}H}{-}OH$ | (D) | $H\overset{Br}{C}{=}\overset{Br}{C}{-}\underset{\text{}}{\overset{C_2H_5}{C}H}{-}OH$ | (VI) |
| $HC{\equiv}C{-}\underset{\text{}}{\overset{C_3H_7}{C}H}{-}OH$ | (E) | $H\overset{Br}{C}{=}\overset{Br}{C}{-}\underset{\text{}}{\overset{C_3H_7}{C}H}{-}OH$ | (VII) |
| $HC{\equiv}C{-}\underset{\text{}}{\overset{C_4H_9}{C}H}{-}OH$ | (F) | $H\overset{Br}{C}{=}\overset{Br}{C}{-}\underset{\text{}}{\overset{C_4H_9}{C}H}{-}OH$ | (VIII) |
| $HC{\equiv}C{-}\underset{\text{}}{\overset{C_8H_{17}}{C}H}{-}OH$ | (G) | $H\overset{Br}{C}{=}\overset{Br}{C}{-}\underset{\text{}}{\overset{C_8H_{17}}{C}H}{-}OH$ | (IX) |
| $HC{\equiv}C{-}\underset{\text{}}{\overset{C_6H_5}{C}H}{-}OH$ | (H) | $H\overset{Br}{C}{=}\overset{Br}{C}{-}\underset{\text{}}{\overset{C_6H_5}{C}H}{-}OH$ | (X) |
| $HC{\equiv}C{-}\underset{CH_3}{\overset{CH_3}{C}}{-}OH$ | (B) | $H\overset{Br}{C}{=}\overset{Br}{C}{-}\underset{CH_3}{\overset{CH_3}{C}}{-}OH$ | (XI) |
| $HC{\equiv}C{-}\underset{C_2H_5}{\overset{CH_3}{C}}{-}OH$ | (I) | $H\overset{Br}{C}{=}\overset{Br}{C}{-}\underset{C_2H_5}{\overset{CH_3}{C}}{-}OH$ | (XII) |
| $HC{\equiv}C{-}\underset{C_4H_9}{\overset{CH_3}{C}}{-}OH$ | (J) | $H\overset{Br}{C}{=}\overset{Br}{C}{-}\underset{C_4H_9}{\overset{CH_3}{C}}{-}OH$ | (XIII) |
| $HC{\equiv}C{-}\underset{C_4H_9}{\overset{C_4H_9}{C}}{-}OH$ | (K) | $H\overset{Br}{C}{=}\overset{Br}{C}{-}\underset{C_4H_9}{\overset{C_4H_9}{C}}{-}OH$ | (XIV) |
| $H_3C{-}C{\equiv}C{-}CH_2OH$ | (L) | $CH_3\overset{Br}{C}{=}\overset{Br}{C}{-}CH_2OH$ | (XV) |
| $H_3C{-}C{\equiv}C{-}CH_2CH_2OH$ | (M) | $CH_3\overset{Br}{C}{=}\overset{Br}{C}{-}CH_2CH_2OH$ | (XVI) |
| $C_6H_5C{\equiv}C{-}(CH_2)_{10}OH$ | (N) | $C_6H_5\overset{Br}{C}{=}\overset{Br}{C}{-}(CH_2)_{10}OH$ | (XVII) |
| $H_{41}C_{20}C{\equiv}C{-}CH_2OH$ | (O) | $H_{41}C_{20}\overset{Br}{C}{=}\overset{Br}{C}{-}CH_2OH$ | (XVIII) |
| $H_3CC{\equiv}C{-}CH_2\overset{CH_3}{C}H{-}OH$ | (P) | $H_3C\overset{Br}{C}{=}\overset{Br}{C}{-}CH_2\overset{CH_3}{C}H{-}OH$ | (XIX) |

-continued

| Acetylenic Alcohol | | Dibromoethylene Derivative | |
|---|---|---|---|
| $C_4H_9C\equiv C-CH_2OH$ | (Q) | $H_9C_4\overset{Br}{C}=\overset{Br}{C}-CH_2OH$ | (XX) |
| $C_6H_5C\equiv C-CH_2OH$ | (R) | $C_6H_5\overset{Br}{C}=\overset{Br}{C}-CH_2OH$ | (XXI) |
| $C_6H_5C\equiv C-CH_2CH_2OH$ | (S) | $C_6H_5\overset{Br}{C}=\overset{Br}{C}-CH_2CH_2OH$ | (XXII) |
| $C_6H_{11}C\equiv C-CH_2OH$ | (T) | $C_6H_{11}\overset{Br}{C}=\overset{Br}{C}-CH_2OH$ | (XXIII) |
| $C_6H_5C\equiv C-\underset{\underset{}{}}{\overset{CH_3}{C}H}-OH$ | (U) | $C_6H_5\overset{Br}{C}=\overset{Br}{C}-\overset{CH_3}{C}H-OH$ | (XXIV) |
| $C_6H_5C\equiv C-\underset{CH_3}{\overset{CH_3}{C}}-OH$ | (V) | $C_6H_5\overset{Br}{C}=\overset{Br}{C}-\underset{CH_3}{\overset{CH_3}{C}}-OH$ | (XXV) |
| $ClC\equiv C-\underset{CH_3}{\overset{CH_3}{C}}-OH$ | (III) | $Cl\overset{Br}{C}=\overset{Br}{C}-\underset{CH_3}{\overset{CH_3}{C}}-OH$ | (XXVI) |
| $BrC\equiv C-\underset{CH_3}{\overset{CH_3}{C}}-OH$ | (IV) | $Br\overset{Br}{C}=\overset{Br}{C}-\underset{CH_3}{\overset{CH_3}{C}}-OH$ | (XXVII) |
| $C_{10}H_7C\equiv CCH_2OH$ | (W) | $C_{10}H_7\overset{Br}{C}=\overset{Br}{C}-CH_2OH$ | (XXVIII) |

EXAMPLE VI

To a solution of 56 parts of propargyl alcohol and 0.1 part of iodine in 300 parts of tetrachloroethylene is slowly passed chlorine gas while exposed to an ultraviolet lamp until 70 parts of chlorine are reacted. The halogenated product is then recovered by distillation and the majority of the product is identical to the 2,3-dichloro-2-propene-1ol of Example I.

b. In a similar manner there is prepared

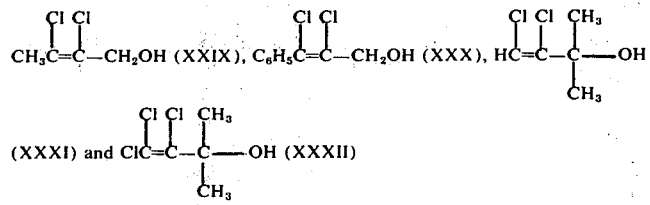

EXAMPLE VII

A mixture of 46 parts of PCl₃, 126 parts of 2,3-dichloro-2-propene-1-ol and 150 parts of toluene is refluxed until no more HCl is evolved from the reaction. The mixture is then allowed to cool to room temperature; then 5 parts of anhydrous sodium carbonate and 3 parts of decolorizing carbon are added to the solution and allowed to stand with stirring for 8 to 24 hours. The solution is then filtered and the filtrate distilled at 0.5 to 14 mm Hg pressure to recover the toluene. The yield of almost colorless residue is 96% of the theoretical amount. The infrared spectra of the product confirm the absence of the band for the —OH group of the alcohol and the presence of the band for the ester group. The product is a viscous oil insoluble in water but soluble in benzene and toluene. The elemental analysis of the product: percent C, 26.95; percent H, 2.24; percent Cl, 52.56; are in close agreement with the theoretical values of C, 26.42; H, 2.20; Cl, 52.02 for P(OCH₂CCl=CHCl)₃. The boiling point of the product is higher than 120° C. at 0.5 mm Hg. Attempts to distill the product at higher pressures, or at higher temperatures at 0.5 mm pressure results in secondary reactions which change the nature of the product, which product, however, is still self-extinguishing. Other triesters of this type having other R groups in place of the —CH₂— and/or having bromine in place of the chlorine or having the tetrachloro or tetrabromo structure can be similarly prepared for use as intermediates in preparing phosphate esters of the present invention. The phosphites are converted to XP(ORCX=CXR')₂ compounds by reaction with PX₃. For example, two moles of P(OCH₂CCl=CHCl)₃ is reacted with one mole of PCl₃ at 100° C. for 3 hours to give three moles of ClP(OCH₂CCl=CHCl)₂.

EXAMPLE VIII

The procedure of Example VII is repeated using 51 parts of $POCl_3$ instead of 46 parts of $PCl_3$ and there is obtained the ester, $PO(OCH_2CCl=CHCl)_3$, which contains approximately 50% chlorine. The reaction with $POCl_3$ is much slower than with $PCl_3$; however, it proceeds very readily if a mole of an hydrogen chloride acceptor, such as triethyl amine or pyridine, is used in the reaction mixture for each mole of liberated hydrogen chloride. Likewise, as indicated in Example VII, other triesters can be similarly prepared having other R groups and halogen composition to prepare intermediates for use in preparing phosphate esters of the present invention. The following procedures (a) and (b) illustrate how these phosphate triesters may be converted to intermediates useful in the preparation of esters of this invention.

a. To 73.85 parts of $P(OCH_2CBr=CHBr)_3$ in 150 parts of toluene are added 13.6 parts of $SO_2Cl_2$ and the mixture is heated at 50° C. for one hour until no more $SO_2$ is liberated. There is obtained an almost quantitative yield of 55.32 parts of

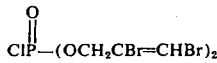

in toluene together with the byproduct, $ClCH_2CBr=CHBr$. This solution can be used as prepared for the synthesis of other derivatives, or it may be distilled to recover toluene and $ClCH_2CBr=CHBr$, leaving as a residue $ClP(O)(OCH_2CBr=CHBr)_2$.

A mixture of 10.15 parts of $P(OCH_2CCl=CHCl)_3$ and 15 parts of $CH_3COOH$ are heated at 100° C. for 2 hours following which it is distilled at 15 mm pressure to recover 42 parts of $CH_3COOCH_2CCl=CHCl$, leaving as a residue 86.2 parts of $HOP(OCH_2CCl=CHCl)_2$ which on analysis is shown to contain 46.4% of Cl compared to a theoretical value of 47.3.

EXAMPLE IX

A mixture of one mole of $CH_2=CHCOOCH_2CH_2PCl_2$ and two moles of 2,3-dichloro-2-propene-1-ol in toluene (100 parts per mole of reagent) is refluxed until no more HCl is evolved from the reaction. The mixture is then allowed to cool to room temperature; then 5 parts of anhydrous sodium carbonate and 3 parts of decolorizing carbon are added to the solution and allowed to stand with stirring for 8 to 24 hours. The solution is then filtered and the filtrate distilled at 0.5 to 14 mm Hg pressure to recover the toluene. The yield of almost colorless residue is 96% of the theoretical amount. The infrared spectra of the product confirm the absence of the band for the —OH group of the alcohol and the presence of the band for the ester group. The elemental analysis conforms to the structure of $CH_2=CHCOOCH_2CH_2P(OCH_2CCl=CHCl)_2$.

Repetition of the foregoing procedure using equivalent amounts respectively of other dihalo acetylenic alcohols gives the following products respectively:

| Dihalo Acetylenic Alcohol | Ester Monomer |
|---|---|
| (b) $CHBr=CBrCH_2OH$ | $CH_2=CHCOOCH_2CH_2P-$ $(OCH_2CBr=CHBr)_2$ |
| (c) $CHCl=CCl(CH_2)_3OH$ | $CH_2=CHCOOCH_2CH_2P-$ $[O(CH_2)_3CCl=CHCl]_2$ |
| (d) $CCl_2=CClCH_2OH$ | $CH_2=CHCOOCH_2CH_2P-$ $(OCH_2CCl=CCl_2)_2$ |
| (e) $CH_3CCl=CClCH_2OH$ | $CH_2=CHCOOCH_2CH_2P-$ $(OCH_2CCl=CClCH_3)_2$ |
| (f) $C_6H_5CBr=CBr(CH_2)_2OH$ | $CH_2=CHCOOCH_2CH_2P-$ $(OCH_2CH_2CBr=CBrC_6H_5)_2$ |
| (g) $CHCl=CClC_6H_{10}OH$ | $CH_2=CHCOOCH_2CH_2P-$ $(OC_6H_{10}CCl=CHCl)_2$ |

Repetition of the foregoing procedure by replacing the phosphinic dichloride with an equivalent amount of other phosphinic dihalides gives the following products respectively:

| Phosphinic Dihalide | Ester Monomer |
|---|---|
| (h) $CH_2=C(CH_3COO(CH_2)_3PCl_2$ | $CH_2=C(CH_3)COO(CH_2)_3P-$ $(OCH_2CCl=CHCl)_2$ |
| (i) $CH_2=C(Cl)COOC_6H_4CH_2PBr_2$ | $CH_2=C(Cl)COOC_6H_4CH_2P-$ $(OCH_2CCl=CHCl)_2$ |
| (j) $CH_2=C(CH_3)COOC_6H_{10}PCl_2$ | $CH_2=C(CH_3)COOC_6H_{10}P-$ $(OCH_2CCl=CHCl)_2$ |
| (k) $CH_2=CHCOOCH(CH_3)CH_2PBr_2$ | $CH_2=CHCOOCH(CH_3)CH_2P-$ $(OCH_2CCl=CHCl)_2$ |
| (l) $CH_2=CHCOOCH(C_3H_7)CH_2CH_2PCl_2$ | $CH_2=CHCOOCH(C_3H_7)CH_2CH_2P-$ $(OCH_2CCl=CHCl)_2$ |

EXAMPLE X

The procedures of Example IX are repeated using in place of the dihaloacetylenic alcohols equivalent amounts respectively of the corresponding tetrahalo alcohols to give the following monomers of this invention:

a. $CH_2=CHCOOCH_2CH_2P(OCH_2CCl_2CHCl_2)_2$
b. $CH_2=CHCOOCH_2CH_2P(OCH_2CBr_2CHBr_2)_2$
c. $CH_2=CHCOOCH_2CH_2P[O(CH_2)_3CCl_2CHCl_2]_2$
d. $CH_2=CHCOOCH_2CH_2P(OCH_2CCl_2CCl_3)_2$
e. $CH_2=CHCOOCH_2CH_2P(OCH_2CCl_2CCl_2CH_3)_2$
f. $CH_2=CHCOOCH_2CH_2P(OCH_2CH_2CBr_2CBr_2C_6H_5)_2$
g. $CH_2=CHCOOCH_2CH_2P(OC_6H_{10}CCl_2CHCl_2)_2$
h. $CH_2=C(CH_3)COO(CH_2)_3P(OCH_2CCl_2CHCl_2)_2$
i. $CH_2=C(Cl)COOC_6H_4CH_2P(OCH_2CCl_2CHCl_2)_2$
j. $CH_2=C(CH_3)COOC_6H_{10}P(OCH_2CCl_2CHCl_2)_2$
k. $CH_2=CHCOOCH(CH_3)CH_2P(OCH_2CCl_2CHCl_2)_2$
l. $CH_2=CHCOOCH(C_3H_7)CH_2CH_2P(OCH_2CCl_2CHCl_2)_2$

EXAMPLE XI

Samples of the various phosphorus esters of Example IV–X are placed individually in a microcrucible and in each case the contents ignited by the flame of a microburner. When the flame is withdrawn, burning stops completely.

EXAMPLE XII

A mixture of 50 parts of methyl methacrylate, 5 parts of $CH_2=CHCOOCH_2CH_2P(OCH_2CBr=CHBr)_2$ and 0.5 parts of benzoyl peroxide is polymerized in a sealed container under nitrogen at 80° C. until a hard polymer is obtained, which is self-extinguishing. Similar self-extinguishing polymers are obtained when, instead of $CH_2=CHCOOCH_2CH_2P(OCH_2CBr=CHBr)_2$ the individual esters of Examples IX–X inclusive are used.

EXAMPLE XIII

The procedure of Example XII is repeated using instead of methyl methacrylate, the monomers styrene, acrylonitrile and vinyl acetate respectively, and self-extinguishing polymers are obtained in each case.

EXAMPLE XIV

Ten parts of $CH_2=CHCOOCH_2CH_2$-$P(OCH_2CBr=CHBR)_2$ are added respectively to each of the following, which are approximately 50% solvents and 50% solids, (a) a clear alkyd varnish, (b) a cellulose acetate-butyrate lacquer, (c) a white-pigment oil modified epoxy paint, and (d) a pigmented urethane-type paint; then films are cast from the mixtures and allowed to dry or cure for four days. Attempts to ignite the resulting films showed in each case that they are self-extinguishing. Similar results are obtained when other esters selected from each of Examples IX and X are similarly tested.

EXAMPLE XV

A mixture of 50 parts $CH_2=CHCOOCH_2CH_2$-$P(OCH_2CBr=CHBr)_2$ 50 parts toluene and 0.5 parts of benzoyl peroxide is polymerized in a sealed container under nitrogen and at 80° C. for 10 hours. The toluene is evaporated to give a solid resin. Five parts of this is mixed with 100 parts respectively of polystyrene, polymethyl methacrylate, polyacrylonitrile, polybutadiene, polyvinylacetate and molded in each case to a hard casting. In each case attempts to ignite each casting showed the product to be self-extinguishing in each case. The procedure is repeated with each of the monomers of Examples IX and X and in each case the product is found to be self-extinguishing.

As shown above the phosphorus-containing esters of this invention are polymerizable by themselves or in mixtures with each other or in mixtures with other vinyl or vinylidene monomers, sometimes referred to herein as vinyl monomers, such as styrenes, i.e., styrene, alphamethylstyrene, vinyl naphthalene, vinyl diphenyl, etc., with acrylates, such as methyl acrylate, methyl methacrylate, butyl acrylate, ethyl chloracrylate, etc., vinyl esters such as vinyl acetate, vinyl benzoate, vinyl butyrate, etc., acrylonitrile, methacrylonitrile, esters of polymerizable dibasic acids such as dimethyl maleate, diethyl fumarate, diallyl phthalate, divinyl azelate, dimethyl itaconate, etc., maleic anhydride, itaconic anhydride, etc.

In producing self-extinguishing copolymers with such copolymerizing monomers, such properties are exhibited with as little as 0.1 percent by weight, preferably at least 1 percent by weight, of a monomer of this invention. In blends of homopolymers or copolymers of these phosphorus-containing esters with other polymers, such as polystyrene, etc., there is advantageously at least 0.1 percent, preferably at least 1 percent by weight, of the product represented by the phosphorus-containing ester portion.

In polymerizing the esters of this invention the various polymerization systems and techniques known in the art may be used, such as free-radical, such as peroxy and azo systems, thermal, radiation and various other systems. For most purposes for which the polymer products are to be used molecular weights of at least 500, preferably at least 1,000, are desirable.

As indicated above and where it may be desired, the polymers can be produced directly with the preparation of the ester by omitting the inhibitor and allowing polymerization to occur simultaneously. If the polymerization has not progressed sufficiently by the time the preparation reaction is completed, heating may be continued at the same or higher temperatures, or catalysts, such as benzoyl peroxide, etc. may be added to complete the polymerization.

While the esters or monomers of this invention have been represented by various formulas, they may also be represented generically by the formulas

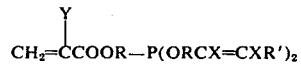

and

wherein $n$ represents zero or one, and the other symbols are as defined above.

Similarly the repeating units in polymers produced from these esters can be represented by the formulas

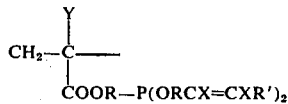

and

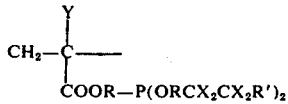

Polymers having repeating units similar to those produced by polymerizing the monomer esters of this invention may also be produced by polymerizing an acrylate portion of the monomer, such as a (hydroxyalkyl) acrylate, or (chloroalkyl) acrylate and reacting the remainder of the ester monomer repeating unit by reactions similar to those used in preparing the monomer.

While certain features of this invention have been described in detail with respect to the various embodiments thereof, it will, of course, be apparent that other modifications may be made within the spirit and scope of this invention, and it is not intended to limit the invention to the exact details shown above except insofar as they are defined in the following claims:

The invention claimed is:

1. A phosphorus-halogen-containing compound having a formula selected from the class consisting of

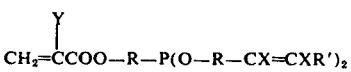

and

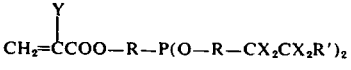

wherein;
- Y represents H, CH₃ or Cl;
- X represents Cl or Br;
- R represents a divalent hydrocarbon radical of 1–20 carbon atoms;
- R' represents H, X or R''; and
- R'' represents a monovalent hydrocarbon radical of 1–20 carbon atoms.

2. The compound of claim 1 in which the formula is

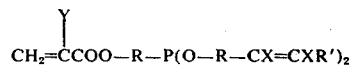

3. The compound of claim 1 wherein X is chlorine.
4. The compound of claim 1 wherein X is bromine.
5. The compound of claim 1 in which R' is hydrogen.
6. The compound of claim 1 having the formula

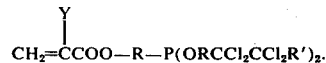

7. The compound of claim 1 wherein Y is CH₃—.
8. The compound of claim 1 wherein R is —CH₂CH₂—.
9. The compound of claim 1 wherein Y is Cl.
10. The compound of claim 1 having the formula

11. The compound of claim 1 having the formula

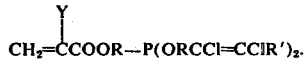

12. The compound of claim 1 having the formula

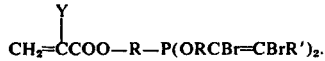

13. The compound of claim 1 having the formula CH₂=CHCOOCH₂CH₂P(OCH₂CCl=CHCl)₂.
14. The compound of claim 1 having the formula CH₂=CHCOOCH₂CH₂P(OCH₂CBr=CHBr)₂.

* * * * *

UNITED STATES PATENT OFFICE
CERTIFICATE OF CORRECTION

Patent No. 3,980,737     Dated Sept. 14, 1976

Inventor(s) Gaetano F. D'Alelio

It is certified that error appears in the above-identified patent and that said Letters Patent are hereby corrected as shown below:

Col. 1, line 54, delete "either" and "or";

Col. 1, line 55, delete "P(O)";

Col. 1, line 66, after formula, insert A.

Signed and Sealed this

Fifteenth Day of February 1977

[SEAL]

Attest:

RUTH C. MASON
Attesting Officer

C. MARSHALL DANN
Commissioner of Patents and Trademarks